(12) United States Patent
Corminboeuf et al.

(10) Patent No.: US 9,676,761 B2
(45) Date of Patent: Jun. 13, 2017

(54) DIFLUOROETHYL-OXAZOLE SUBSTITUTED BRIDGED SPIRO[2.4]HEPTANE DERIVATIVES AS ALX RECEPTOR AGONISTS

(71) Applicant: ACTELION PHARMACEUTICALS LTD, Allschwil (CH)

(72) Inventors: Olivier Corminboeuf, Allschwil (CH); Sylvaine Cren, Allschwil (CH); Davide Pozzi, Allschwil (CH)

(73) Assignee: ACTELION PHARMACEUTICALS, LTD., Allschwil (CH)

( * ) Notice: Subject to any disclaimer, the term of this patent is extended or adjusted under 35 U.S.C. 154(b) by 0 days.

(21) Appl. No.: 14/757,491

(22) PCT Filed: Jun. 24, 2014

(86) PCT No.: PCT/EP2014/063243
§ 371 (c)(1),
(2) Date: Dec. 23, 2015

(87) PCT Pub. No.: WO2014/206966
PCT Pub. Date: Dec. 31, 2014

(65) Prior Publication Data
US 2016/0289221 A1    Oct. 6, 2016

(30) Foreign Application Priority Data
Jun. 25, 2013    (WO) .................. PCT/IB2013/055220

(51) Int. Cl.
*C07D 413/12*    (2006.01)

(52) U.S. Cl.
CPC .................................. *C07D 413/12* (2013.01)

(58) Field of Classification Search
CPC .................................................... C07D 413/12
USPC .......................................... 546/15; 514/278
See application file for complete search history.

(56) References Cited

FOREIGN PATENT DOCUMENTS

| WO | WO 95/02587 A1 | 1/1995 |
|---|---|---|
| WO | WO 03/082314 A2 | 10/2003 |
| WO | WO 2005/047899 A2 | 5/2005 |
| WO | WO 2009/077954 A1 | 6/2009 |
| WO | WO 2009/077990 A1 | 6/2009 |
| WO | WO 2010/134014 A1 | 11/2010 |
| WO | WO 2010/143116 A1 | 12/2010 |
| WO | WO 2010/143158 A1 | 12/2010 |
| WO | WO 2011/163502 A1 | 12/2011 |
| WO | WO 2012/066488 A2 | 5/2012 |
| WO | WO 2012/077049 A1 | 6/2012 |
| WO | WO 2012/077051 A1 | 6/2012 |
| WO | WO 2013/009543 A1 | 1/2013 |
| WO | WO 2013/171687 A1 | 11/2013 |
| WO | WO 2013/171694 A1 | 11/2013 |
| WO | WO 2014/138037 A1 | 9/2014 |
| WO | WO 2014/138046 A1 | 9/2014 |
| WO | WO 2014/206966 A1 | 12/2014 |
| WO | WO 2015/019325 A1 | 2/2015 |

OTHER PUBLICATIONS

Bannenberg, "Anti-Inflammatory Actions of Lipoxins", Expert Opinion on Therapeutic Patent, 17(6), 591-605, 2007.
Burli et al, "Potent hFPRL1 (ALXR) Agonists as Potential Anti-Inflammatory Agents", Bioorganic & Medicinal Chemistry Letters, 16(4), 3713-3718, 2006.
Celik et al, "Lipoxin A4 Levels in Asthma: Relation with Disease Severity and Aspirin Sensitivity", Clinical and Experimental Allergy, 37, 1494-1501, 2007.
Chiang et al, "The Lipoxin Receptor ALX: Potent Ligand-Specific and Stereoselective Actions in Vivo", Pharmacological Reviews, 58(3), 463-487, 2006.
Edwards et al, "Integration of Virtual Screening with High-Throughput Flow Cytometry to Identify Novel Small Molecule Formylpeptide Receptor Antagonists", Molecular Pharmacology, 68(5), 1301-10, 2005.
Gewirtz et al, "Mechanisms of Active Intestinal Inflammation and Potential Down-Regulation Via Lipoxins", Adv Exp Med Biol, 507, 229-36, 2002.
Gronert et al, "A Role for the Mouse 12/15-Lipoxygenase Pathway in Promoting Epithelial Wound Healing and Host Defense", The Journal of Biological Chemistry, 280(15), 15267-15278, 2005.
Gronert, "Lipoxins in the Eye and Their Role in Wound Healing", Prostaglandins Leukotrienes and Essential Fatty Acids, 73, 221-229, 2005.
Jin et al, "Posttreatment with Aspirin-Triggered Lipoxin A4 Analog Attenuates Lipopolysaccharide-Induced Acute Lung Injury in Mice: The Role of Heme Oxygenase-1", International Anesthesia Research Society, 104(2), 369-377, 2007.
Karp et al, "Defective Lipoxin-Mediated Anti-Inflammatory Activity in the Cystic Fibrosis Airway", Nature Immunology, 5(4), 388-392, 2004.
Le et al, "Biologically Active Peptides Interacting with the G Protein-Coupled Formylpeptide Receptors", Protein and Peptide Letters, 14, 846-853, 2007.

(Continued)

*Primary Examiner* — Kahsay Habte
(74) *Attorney, Agent, or Firm* — Arent Fox LLP

(57) ABSTRACT

The present invention relates to difluoroethyl-oxazole substituted bridged spiro[2.4] heptane derivatives of formula (I),

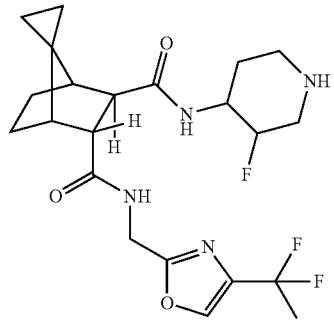

wherein the substituents at the piperidine ring are in trans-arrangement, their preparation and their use as pharmaceutically active compounds.

7 Claims, No Drawings

(56) References Cited

OTHER PUBLICATIONS

Levy et al, "Lipoxin A4 Stable Analogs Reduce Allergic Airway Responses via Mechanisms Distinct from CysLT1 Receptor Antagonism", The FASEB Journal, 21, 3877-3884, 2007.

Levy et al, "Multi-Pronged Inhibition of Airway Hyper-Responsiveness and Inflammation by Lipoxin A4", Nature Medicine, 8(9), 1018-1023, 2002.

Mamiya et al, "[Gly14]-Humanin Improved the Learning and Memory Impairment Induced by Scopolamine in Vivo", British Journal of Pharmacology, 134, 1597-1599, 2001.

Miao et al, "S14G-Humanin Ameliorates AB25-35-Induced Behavioral Deficits by Reducing Neuroinflammatory Responses and Apoptosis in Mice", Neuropeptides, 42, 557-567, 2008.

Planaguma et al, "Airway LXA4 Generation and LXA4 Receptor Expression are Decreased in Severe Asthma", Am J Respir Crit Care Med, 178, 574-582, 2008.

Schwab et al, "Lipoxins and New Lipid Mediators in the Resolution of Inflammation", Current Opinion in Pharmacology, 414-420(6), 2006.

Sodin-Semrl et al, "Lipoxin A4 Counteracts Synergistic Activation of Human Fibroblast-Like Synoviocytes", International Journal of Immunopathology and Pharmacology, 17(1), 15-25, 2004.

Stahl et al, "Handbook of Pharmaceutical Salts Properties", International Union of Pure and Applied Chemistry (IUPAC) Selection and Use, 2008.

Williams et al, "Pharmaceutical Manufacturing", Remington, The Science and Practice of Pharmacy, 21st Edition Part 5, 2005.

Wouters et al, "Pharmaceutical Salts and Co-Crystals", RSC Publishing, 2012.

Yazawa et al, "B Amyloid Peptide (AB42) is Internalized via the G-Protein-Coupled Receptor FPRL1 and Forms Fibrillar Aggregates in Macrophages1", The FASEB Journal, 15, 2454-2462, 2001.

Ying et al, "Humanin, a Newly Identified Neuroprotective Factor, Uses the G Protein-Coupled Formylpeptide Receptor-Like-1 as a Functional Receptor1", The Journal of Immunology, 172, 7078-7085, 2004.

Zhang et al, "BML-111, a Lipoxin Receptor Agonist, Modulates the Immune Response and Reduces the Severity of Collagen-Induced Arthiritis", Inflammation Research, 57, 157-162, 2008.

International Search Report of PCT/EP2014/063243 dated Aug. 29, 2014.

DIFLUOROETHYL-OXAZOLE SUBSTITUTED BRIDGED SPIRO[2.4]HEPTANE DERIVATIVES AS ALX RECEPTOR AGONISTS

CROSS-REFERENCE TO RELATED APPLICATIONS

This application is a National Stage entry of International Application No. PCT/EP2014/063243, filed Jun. 24, 2014, which claims priority to International Application No. PCT/IB2013/055220, filed Jun. 25, 2013. The disclosures of the prior applications are hereby incorporated in their entirety by reference.

The present invention relates to difluoroethyl-oxazole substituted bridged spiro[2.4] heptane derivatives of formula (I) and their use as pharmaceuticals. The invention also concerns related aspects including processes for the preparation of the compounds, pharmaceutical compositions containing one or more compounds of formula (I), and especially their use as ALX receptor (ALXR) agonists.

ALXR (alias Lipoxin A4 Receptor, FPRL1, FPR2; disclosed in WO2003/082314 as nucleotide sequence SEQ ID NO:1 and amino acid sequence SEQ ID NO:2) is a member of the G-protein coupled receptor family. ALXR was found to mediate calcium mobilisation in response to high concentration of the formyl-methionine-leucyl-phenylalanine peptide. Furthermore, a lipid metabolite, lipoxin A4 (LXA4), and its analogues, were found to bind ALXR with high affinity and increase arachidonic acid production and G-protein activation in ALXR transfected cells (Chiang et al., Pharmacol. Rev., 2006, 58, 463-487). The effects of LXA4 have been evaluated in a variety of animal models of diseases; and LXA4 was demonstrated to have potent anti-inflammatory and pro-resolution activities. The disease models where LXA4, or derivatives, or stable analogs, demonstrated in vivo activities are for example dermal inflammation, dorsal air pouch, ischemia/reperfusion injury, peritonitis, colitis, mesangioproliferative nephritis, pleuritis, asthma, cystic fibrosis, sepsis, corneal injury, angiogenesis, periodontitis, carrageenan-induced hyperalgesia, and graft-vs-host disease (GvHD) (Schwab and Serhan, Current Opinion in Pharmacology, 2006, 414-420). Lipoxin A4 inhibited IL-6 expression in human fibroblast-like synoviocytes (Sodin-Semrl et al, *Int J Immunopathol Pharmacol* (2004) 17:15-25) and a stable FPR2 agonist, BML-111, reduced the severity of collagen-induced arthritis (Zhang et al., (2008) *Inflamm Res* 57:157-162) demonstrating a possible use of FPR2 agonists in the treatment of rheumatoid arthritis. Mice with acute lung injury (ALI) showed reduced pulmonary inflammation when treated with stable lipoxin A4 (Jin et al., (2007) *Anesth Analg* 104:369-377). Lower lipoxin A4 levels in severe asthma (Celik et al., (2007) *Clin Exp Allergy* 37:1494-1501; Planaguma et al, (2008) *Am J Respir Crit Care Med* 178:574-582) and improvement of asthma responses in animal models by stable lipoxin A4 analogs (Levy et al., (2002) *Nat Med* 8:1018-1023; Levy et al., (2007) *FASEB J* 21:3877-3884) have been described. In cystic fibrosis it was shown, that the levels of pulmonary lipoxin A4 are decreased both in the lung of cystic fibrosis patients and in animal models of the disease (Karp et al., (2004) *Nat Immunol* 5:388-392); treatment with a stable lipoxin analog improved inflammatory cell accumulation within the diseased lung and reduced body weight loss in the same animals (Karp et al., (2004) *Nat Immunol* 5:388-392). Topical treatment with lipoxin A4 increases re-epithelization and decreases inflammation of the dry corneal surface (Gronert, (2005) *Prostaglandins Leukot Essent Fatty Acids* 73:221-229; Gronert et al., (2005) *J Biol Chem* 280:15267-15278) demonstrating a possible use of FPR2 agonists in the treatment of keratoconjunctivitis sicca. Oral administration of lipoxin A4 analogs reduced the severity of colitis in a mouse model of inflammatory bowel disease (Gewirtz et al., (2002) *Eicosanoids and other Bioactive Lipids in Cancer, Inflammation, and Radiation Injury*, Kluwer Academic/Plenum Publishers, 229-236).

ALXR was also identified as a functional receptor of a various number of peptides, including a fragment of the prion protein, a peptide derived from gp120 of the Human Immunodeficiency Virus (HIV)-$1_{LAI}$ strain, and amyloid-beta 1-42 (Ab42) (for review, Le et al., Protein Pept Lett., 2007, 14, 846-853), and has been suggested to participate in the pathogenesis of Alzheimer's Disease (AD) in several crucial ways (Yazawa et al., FASEB J., 2001, 15, 2454-2462). Activation of ALXR on macrophages and microglial cells initiates a G protein-mediated signalling cascade that increases directional cell migration, phagocytosis, and mediator release. These events may account for the recruitment of mononuclear cells to the vicinity of senile plaques in the diseased areas of AD brain where Ab42 is overproduced and accumulated. Although accumulation of leukocytes at the sites of tissue injury may be considered an innate host response aimed at the clearance of noxious agents, activated mononuclear phagocytes also release a variety of substances such as superoxide anions that may be toxic to neurons. Thus, ALXR may mediate pro-inflammatory responses elicited by Ab42 in AD brain and exacerbate disease progression. Further, humanin is a high-affinity ligand for ALXR and is neuroprotective in models of Alzheimer's Disease (Mamiya et al., (2001) *Br J Pharmacol* 134:1597-1599; Ying et al., (2004) *J Immunol* 172:7078-7085; Miao et al., (2008) *Neuropeptides* 42:557-567).

The biological properties of ALXR agonists include, but are not limited to, monocyte/macrophage/microglia/dendritic cell migration/activation, neutrophil migration/activation, regulation of lymphocyte activation, proliferation and differentiation, regulation of inflammation, regulation of cytokine production and/or release, regulation of proinflammatory mediator production and/or release, regulation of immune reaction.

The present invention provides difluoroethyl-oxazole substituted bridged spiro[2.4]heptane derivatives, which are non-peptide agonists of human ALX receptor. Other bridged spiro[2.4]heptane derivatives with agonistic activity on human ALX receptor have been disclosed in WO 2010/134014, WO2011/163502, WO2012/066488, WO2013/009543, WO2013/171694 and WO2013/171687. Different bridged spiro[2.4]heptane derivatives have been disclosed in WO95/02587. The compounds are useful for the prevention or treatment of diseases, which respond to the modulation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the prevention or treatment of autoimmune diseases and for the modulation of immune responses (especially those elicited by vaccination).

Various embodiments of the invention are presented hereafter:

1) The present invention relates to compounds of formula (I),

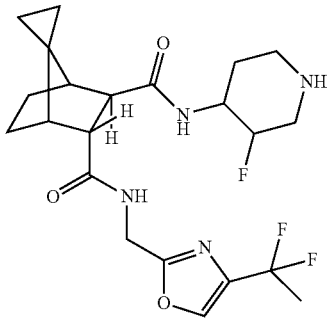

(I)

wherein the substituents at the piperidine ring are in trans-arrangement;
and to the salts (in particular pharmaceutically acceptable salts) of such compounds.

For avoidance of any doubt, the configuration of compounds of formula (I) according to embodiment 1) is such that the two amide substituents at the bridged spiro[2.4]heptane moiety are in trans-arrangement and that the cyclopropyl-moiety is in relative proximity to the piperidine-substituted amide (exo-position).

For avoidance of any doubt, compounds of formula (I) are denominated in analogy to the following example:
the pure stereoisomer of structure

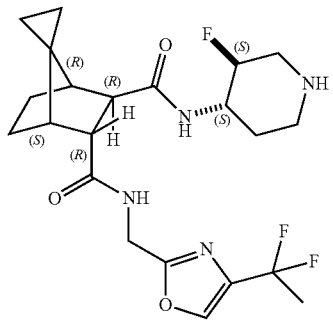

is denominated
(1S,2R,3R,4R)—N²—((4-(1,1-difluoroethyl)oxazol-2-yl)methyl)—N³—((3S,4S)-3-fluoropiperidin-4-yl)spiro[bicyclo[2.2.1]heptane-7,1'-cyclopropane]-2,3-dicarboxamide.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

2) A preferred embodiment of the invention relates to compounds of formula (I) according to embodiment 1) which are also compounds of formula (I$_{ST1}$),

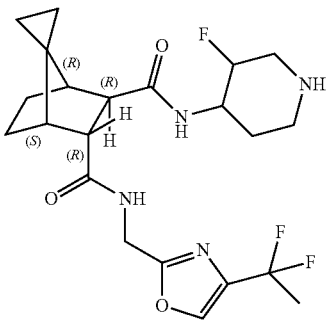

(I$_{ST1}$)

wherein the substituents at the piperidine ring are in trans-arrangement;
and to the salts (in particular pharmaceutically acceptable salts) of such compounds.

3) A preferred compound of formula (I) as defined in embodiment 1) is:
(1S,2R,3R,4R)—N²—((4-(1,1-difluoroethyl)oxazol-2-yl)methyl)—N³—((3S,4S)-3-fluoropiperidin-4-yl)spiro[bicyclo[2.2.1]heptane-7,1'-cyclopropane]-2,3-dicarboxamide;
or a salt (in particular a pharmaceutically acceptable salt) of such compound.

4) Another preferred compound of formula (I) as defined in embodiment 1) is:
(1S,2R,3R,4R)—N²—((4-(1,1-difluoroethyl)oxazol-2-yl)methyl)—N³—((3R,4R)-3-fluoropiperidin-4-yl)spiro[bicyclo[2.2.1]heptane-7,1'-cyclopropane]-2,3-dicarboxamide;
or a salt (in particular a pharmaceutically acceptable salt) of such compound.

The present invention also includes isotopically labelled, especially ²H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially ²H (deuterium) labelled compounds of formula (I) and salts thereof are within the scope of the present invention. Substitution of hydrogen with the heavier isotope ²H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008 and 'Pharmaceutical Salts and Co-crystals', Johan Wouters and Luc Quéré (Eds.), RSC Publishing, 2012.

Where the plural form is used for compounds, salts, pharmaceutical compositions, diseases and the like, this is intended to mean also a single compound, salt, pharmaceutical composition, disease or the like.

The compounds of formula (I) according to any one of embodiments 1) to 4), or pharmaceutically acceptable salts thereof, are suitable for use as medicaments. In particular, compounds of formula (I) modulate the ALX receptor, i.e. they act as ALX receptor agonists, and are useful for the prevention or treatment of diseases which respond to the activation of the ALX receptor such as inflammatory diseases, obstructive airway diseases, allergic conditions, HIV-mediated retroviral infections, cardiovascular disorders, neuroinflammation, neurological disorders, pain, prion-mediated diseases, leukemias and amyloid-mediated disorders (especially Alzheimer's disease); in addition they are useful for the modulation of immune responses (especially those elicited by vaccination).

In particular, the compounds of formula (I) according to any one of embodiments 1) to 4), or pharmaceutically acceptable salts thereof, are suitable for the prevention or treatment of diseases selected from inflammatory diseases, obstructive airway diseases and allergic conditions.

Inflammatory diseases, obstructive airway diseases and allergic conditions include, but are not limited to, one, several or all of the following groups of diseases and disorders:

1) Acute lung injury (ALI); adult/acute respiratory distress syndrome (ARDS); chronic obstructive pulmonary, airway or lung disease (COPD, COAD or COLD), including chronic bronchitis or dyspnea associated therewith; emphysema; as well as exacerbation of airway hyper reactivity consequent to other drug therapy, in particular other inhaled drug therapy. Especially, inflammatory diseases, obstructive airway diseases and allergic conditions include COPD, COAD and COLD.
2) Further inflammatory diseases, obstructive airway diseases and allergic conditions include bronchitis of whatever type or genesis.
3) Further inflammatory diseases, obstructive airway diseases and allergic conditions include bronchiectasis, and pneumoconiosis of whatever type or genesis.
4) Further inflammatory diseases, obstructive airway diseases and allergic conditions include asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection.
5) In a further embodiment the compounds of formula (I) according to any one of embodiments 1) to 4), or pharmaceutically acceptable salts thereof, are particularly suitable for the prevention or treatment of inflammatory diseases. Inflammatory diseases include one, several or all of the following groups of diseases and disorders:
    5a) In particular, inflammatory diseases refer to neutrophil related disorders, especially neutrophil related disorders of the airway including hyper-neutrophilia as it affects the airway and/or lungs. Further neutrophil related disorders also include gingivitis, periodontitis, glomerulonephritis, and cystic fibrosis.
    5b) Further inflammatory diseases include skin diseases such as psoriasis, contact dermatitis, atopic dermatitis, dermatitis herpetiformis, scleroderma, hypersensitivity angiitis, urticaria, lupus erythematosus, dicoid lupus and epidermolysis.
    5c) Further inflammatory diseases also relate to diseases or conditions having an inflammatory component. Diseases or conditions having an inflammatory component include, but are not limited to, diseases and conditions affecting the eye such as uveitis (anterior, intermediate and posterior), Behçet syndrome uveitis, conjunctivitis, keratoconjunctivitis sicca, Sjögren syndrome keratoconjunctivitis sicca, and vernal conjunctivitis; diseases affecting the nose including rhinitis and allergic rhinitis (and especially allergic rhinitis); and inflammatory diseases in which autoimmune reactions are implicated or which have an autoimmune component or aetiology, such as systemic lupus erythematosus, ankylosing spondylitis, Behçet syndrome, Sjögren syndrome, polychondritis, scleroderma, Wegener granulamatosis, giant cell arteritis, neutrophilic dermatoses, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine opthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis.
    5d) Further inflammatory diseases in which autoimmune reactions are implicated or which have an autoimmune component or aetiology include rheumatoid arthritis, Hashimoto's thyroid and diabetes type I or II.

Further, the compounds of formula (I) according to any one of embodiments 1) to 4), or pharmaceutically acceptable salts thereof, are suitable for the prevention or treatment of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation, particularly in the treatment of acute or chronic allo- and xenograft rejection or in the transplantation of insulin producing cells, e.g. pancreatic islet cells.

Further, the compounds of formula (I) according to any one of embodiments 1) to 4), or pharmaceutically acceptable salts thereof, are suitable for the prevention or treatment of HIV-mediated retroviral infections. HIV-mediated retroviral infections include, but are not limited to, one, several or all of the groups of diseases and disorders caused by HIV-1 and HIV-2 strains such as GUN-4v, GUN-7wt, AG204, AG206, AG208, HCM305, HCM308, HCM342, mSTD104, and HCM309.

Further, the compounds of formula (I) according to any one of embodiments 1) to 4), or pharmaceutically acceptable salts thereof, are suitable for the prevention or treatment of cardiovascular disorders. Cardiovascular disorders refer to one or more disease states of the cardiovascular tree (including the heart) and to diseases of dependent organs. Disease states of the cardiovascular tree and diseases of dependent organs include, but are not limited to, disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; toxic, drug-induced, and metabolic (including hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Further, the compounds of formula (I) according to any one of embodiments 1) to 4), or pharmaceutically acceptable salts thereof, are suitable for the prevention or treatment of neuroinflammation. Neuroinflammation refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and Post Synaptic Density-95 Protein (PSD-95), components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid β deposition of amyloid plaques.

Further, the compounds of formula (I) according to any one of embodiments 1) to 4), or pharmaceutically acceptable salts thereof, are suitable for the prevention or treatment of neurological disorders. In particular, neurological disorders include, but are not limited to, epilepsy, stroke, cerebral ischemia, cerebral palsy, relapsing remitting multiple sclerosis, progressive multiple sclerosis, neuromyelitis optica, clinically isolated syndrome, Alpers' disease, amyotrophic lateral sclerosis (ALS), senile dementia, dementia with Lewy bodies, Rett syndrome, spinal cord trauma, traumatic brain injury, trigeminal neuralgia, chronic inflammatory demyelinating polyneuropathy, Guillain-Barré syndrome, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea.

Further, the compounds of formula (I) according to any one of embodiments 1) to 4), or pharmaceutically acceptable salts thereof, are suitable for the prevention or treatment of pain. Pain includes, but is not limited to, neuropathic pain exemplified by conditions such as diabetic neuropathy, postherpetic neuralgia, trigeminal neuralgia, painful diabetic polyneuropathy, post-stroke pain, post-amputation pain, myelopathic or radiculopathic pain, atypical facial pain and causalgia-like syndromes.

Further, the compounds of formula (I) according to any one of embodiments 1) to 4), or pharmaceutically acceptable salts thereof, are suitable for the prevention or treatment of prion-mediated diseases. Prion-mediated diseases, also known as transmissible spongiform encephalopathies (TSEs), include, but are not limited to, kuru, Gerstmann-Sträussler-Scheinker syndrome (GSS), Fatal Familial Insomnia (FFI) and Creutzfeldt-Jakob Disease (CJD).

Further, the compounds of formula (I) according to any one of embodiments 1) to 4), or pharmaceutically acceptable salts thereof, are suitable for the treatment of amyloid-mediated disorders. Amyloid-mediated disorders are defined as diseases and disorders, that are caused by or associated with amyloid or amyloid-like proteins. Diseases and disorders caused by or associated with amyloid or amyloid-like proteins include, but are not limited to, Alzheimer's Disease (AD), including diseases or conditions characterized by a loss of cognitive memory capacity such as, for example, mild cognitive impairment (MCI); dementia with Lewy bodies; Down's syndrome; cerebral hemorrhage with amyloidosis. In another embodiment, diseases and disorders caused by or associated with amyloid or amyloid-like proteins include progressive supranuclear palsy, amyloid light chain amyloidosis, familial amyloid neuropathies, multiple sclerosis, Creutzfeld Jakob disease, Parkinson's disease, HIV-related dementia, Amyotrophic Lateral Sclerosis (ALS), inclusion-body myositis (IBM), Adult Onset Diabetes, and senile cardiac amyloidosis.

Further, the compounds of formula (I) according to any one of embodiments 1) to 4), or pharmaceutically acceptable salts thereof, are suitable for the modulation of immune responses. The modulation of immune responses includes, but is not limited to, methods based on the administration to a subject a composition of at least one antigen and at least one compound of formula (I) according to any one of embodiments 1) to 4), or pharmaceutically acceptable salts thereof. In some cases, the antigen-containing composition is administered first, followed by administration of a composition of at least one compound of formula (I) according to any one of embodiments 1) to 4), or pharmaceutically acceptable salts thereof. In other cases, the antigen-containing composition is administered last. The different compositions may be administered simultaneously, closely in sequence, or separated in time. Those methods and compositions are provided for therapeutic and prophylactic immunisation (i.e., the deliberate provocation, enhancement, intensification or modulation of an adaptative and/or innate immune response). Particular advantages may include one or more of the following:
1) An accelerated immune response following administration of at least one compound of formula (I) according to any one of embodiments 1) to 4), or pharmaceutically acceptable salts thereof, and the antigen, as compared to sole administration of the antigen;
2) A greater sensitivity to small amounts of antigen (e.g., toxin or pathogen) or antigens that do not habitually induce strong immune responses; and
3) More effective anti-tumor therapies.

Further, the compounds of formula (I) according to any one of embodiments 1) to 4), or pharmaceutically acceptable salts thereof, are suitable for the prevention or treatment of cystic fibrosis, pulmonary fibrosis, pulmonary hypertension, wound healing, diabetic nephropathy, reduction of inflammation in transplanted tissue, inflammatory diseases caused by pathogenic organisms.

Especially, compounds of formula (I) according to any one of embodiments 1) to 4), or pharmaceutically acceptable salts thereof, are suitable for the prevention or treatment of diseases selected from one, several or all of the following groups of diseases and disorders:
1) Inflammatory diseases, obstructive airway diseases and allergic conditions such as acute lung injury (ALI); adult/acute respiratory distress syndrome (ARDS); chronic obstructive pulmonary, airway or lung disease (COPD, COAD or COLD), including chronic bronchitis or dyspnea associated therewith; and asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection;

2) Inflammatory diseases such as neutrophil related disorders, especially neutrophil related disorders of the airway including hyper-neutrophilia as it affects the airway and/or lungs; periodontitis; glomerulonephritis; cystic fibrosis; and skin diseases such as psoriasis, contact dermatitis, atopic dermatitis, dermatitis herpetiformis, scleroderma, hypersensitivity angiitis, urticaria, lupus erythematosus, and epidermolysis;

3) Diseases having an inflammatory component such as diseases and conditions affecting the eye such as conjunctivitis, keratoconjunctivitis sicca, and vernal conjunctivitis; inflammatory disease in which autoimmune reactions are implicated or which have an autoimmune component or aetiology; and autoimmune inflammatory bowel disease (e.g. ulcerative colitis and Crohn's disease);

4) HIV-mediated retroviral infections such as diseases and disorders caused by HIV-1 and HIV-2 strains such as GUN-4v, GUN-7wt, AG204, AG206, AG208, HCM305, HCM308, HCM342, mSTD104, and HCM309;

5) Neuroinflammation which refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as amyloid β deposition of amyloid plaques;

6) Neurological disorders such as stroke, cerebral ischemia, Alzheimer's disease, and Parkinson's disease;

7) Prion-mediated diseases, also known as transmissible spongiform encephalopathies (TSEs), such as kuru, Gerstmann-Sträussler-Scheinker syndrome (GSS), Fatal Familial Insomnia (FFI) and Creutzfeldt-Jakob Disease (CJD);

8) Amyloid-mediated disorders;

9) Cystic fibrosis, wound healing and inflammatory diseases caused by pathogenic organisms.

Most preferably, compounds of formula (I) according to any one of embodiments 1) to 4), or pharmaceutically acceptable salts thereof, are suitable for the prevention or treatment of diseases selected from the group consisting of acute lung injury (ALI); asthma; cystic fibrosis; keratoconjunctivitis sicca; inflammatory bowel disease; rheumatoid arthritis; and Alzheimer's Disease.

The invention also relates to the use of a compound of formula (I) according to any one of embodiments 1) to 4) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 4).

A pharmaceutical composition according to the present invention contains at least one compound of formula (I) according to any one of embodiments 1) to 4) (or a pharmaceutically acceptable salt thereof) as the active agent and optionally carriers and/or diluents and/or adjuvants.

The compounds of formula (I) according to any one of embodiments 1) to 4) and their pharmaceutically acceptable salts can be used as medicaments, e.g. in the form of pharmaceutical compositions for enteral (such as especially oral) or parenteral (including topical application or inhalation) administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 4), or a pharmaceutically acceptable salt thereof.

Any reference to a compound of formula I or $I_{ST1}$ in this text is to be understood as referring also to the salts (and especially the pharmaceutically acceptable salts) of such compounds, as appropriate and expedient. The preferences indicated for the compounds of formula I of course apply mutatis mutandis to the compounds of formula $I_{ST1}$ as well as to the salts and pharmaceutically acceptable salts of the compounds of formula I or of formula $I_{ST1}$. The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (rt) as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The compounds of formula (I) can be manufactured by the methods given in the Examples or by analogous methods. Optimum reaction conditions may vary with the particular reactants or solvents used, but such conditions can be determined by a person skilled in the art by routine optimisation procedures.

Experimental Part

Abbreviations (As Used Herein and in the Description Above)

Ac acetyl
AcCN acetonitrile
AcOH acetic acid
aq. aqueous

Boc tert-butoxycarbonyl
bp boiling point
ca. circa
COAD chronic obstructive airway disease
COLD chronic obstructive lung disease
COPD chronic obstructive pulmonary disease
DAD diode array detector
DEA diethylamine
Deoxo-Fluor bis(2-methoxyethyl)aminosulfur trifluoride
DIPEA diisopropylethylamine
DMEM dulbecco's modified eagle's medium
DMF dimethylformamide
DMSO dimethylsulfoxide
EA ethyl acetate
$EC_{50}$ half maximal effective concentration
EDC N-(3-dimethylaminopropyl)-N'-ethyl-carbodiimide
ELSD evaporative light-scattering detection
eq. equivalent(s)
Et ethyl
$Et_2O$ diethylether
$Et_3N$ triethylamine
EtOH ethanol
FC flash column chromatography on silica gel
FLIPR fluorescence imaging plate reader
FPRL1 formyl-peptide receptor like-1
FPRL2 formyl-peptide receptor like-2
h hour(s)
Hank's BSS hanks' balanced salt solution
HEPES 4-(2-hydroxyethyl)-1-piperazineethanesulfonic acid
hept heptane
HIV human immunodeficiency virus
HOBt hydroxybenzotriazole
HPLC high performance liquid chromatography
IpAc isopropyl acetate
LC-MS liquid chromatography-mass spectrometry
lem emission wavelength
lex excitation wavelength
Me methyl
MeOH methanol
min minute(s)
(m)M (milli)molar
µM micromolar
MPLC medium pressure liquid chromatography
MS mass spectrometry
nm nanometer
nM nanomolar
NMR nuclear magnetic resonance
org. organic
p para
PG protecting group
rf retention factor
rpm rotation per minute
rt room temperature
sat. saturated
TFA trifluoroacetic acid
THF tetrahydrofuran
TLC thin layer chromatography
TMS trimethyl-silyl
$t_R$ retention time
UV ultra violet
Vis visible
I. Chemistry
General. All temperatures are stated in degrees Celsius (° C.). Unless otherwise indicated, the reactions take place at rt.

Analytical thin layer chromatography (TLC) was performed with 0.2 mm plates: Merck, Silica gel 60 $F_{254}$. Preparative thin layer chromatography (TLC) was performed with 0.2 or 0.5 mm plates: Merck, Silica gel 60 $F_{254}$. Detection was done with UV or with a solution of $KMnO_4$ (3 g), $K_2CO_3$ (20 g), NaOH 5% (3 mL) and $H_2O$ (300 mL) with subsequent heating.

Flash column chromatography (FC) and filtration were performed using silica gel 60 Merck (0.063-0.200 mm) or Macherey-Nagel silica gel (0.063-0.200 mm): elution with EA, $Et_2O$, hept, hexane, petroleum ether, $CH_2Cl_2$, $CHCl_3$, MeOH, $NH_4OH$ or mixtures thereof.

MPLC were performed using isolute® SPE Flash SI II columns from international sorbent technology, elution with EA, $Et_2O$, hept, hexane, $CH_2Cl_2$, $CHCl_3$, MeOH, $NH_4OH$ or mixtures thereof.

LC-MS-conditions 01 (if not indicated otherwise): Analytical: Thermo Finnigan MSQ Plus MS with Agilent 1100 Binary Pump and DAD. Column: Zorbax SB-AQ 5 µm, 4.6×50 mm ID from Agilent Technologies. Eluents: A: $H_2O$+0.04% TFA; B: $CH_3CN$; Gradient: 5% B→95% B over 1 min. Flow: 4.50 mL/min. Detection: UV/Vis and/or ELSD, and MS, $t_R$ is given in min.

LC-MS-conditions 02 (if not indicated otherwise): Analytical: Dionex HPG-3000 Binary Pump, MS: Thermo MSQ MS, DAD: dionex 3000RS, ELSD: Sedere Sedex 85. Column: Atlantis T3, 5 um, 4.6×30 mm from Waters, thermostated in the Dionex TCC-3200 compartment. Eluents: A: $H_2O$+0.04% TFA; B: $CH_3CN$; Gradient: 5% B→95% B over 1.00 min. Flow: 4.5 mL/min. Detection: UV/Vis and/or ELSD, and MS, $t_R$ is given in min.

LC-MS-conditions 03 (if not indicated otherwise): Analytical. Pump: Dionex HPG-3200RS, MS: Thermo MSQ Plus, DAD: Dionex DAD-3000RS, ELSD: Sedere Sedex 85. Column: Zorbax SB-AQ 3.5 µm, 4.6×50 mm ID from Agilent Technologies, thermostated in the Dionex TCC-3200 compartment. Eluents: A: $H_2O$+0.04% TFA; B: $CH_3CN$. Method: Gradient: 5% B→95% B over 1.00 min. Flow: 4.5 mL/min. Detection: UV/Vis and/or ELSD, and MS, $t_R$ is given in min.

LC-MS-conditions 04 (if not indicated otherwise): Analytical. Pump: Agilent _G4220A_, MS: Thermo MSQ Plus, DAD: Agilent _G4212A_, ELSD: Sedere Sedex 90. Column: Zorbax SB-AQ 3.5 µm, 4.6×50 mm ID from Agilent Technologies, thermostated in the Dionex TCC-3200 compartment. Eluents: A: $H_2O$+0.04% TFA; B: $CH_3CN$. Eluent MakeUp: $CH_3CN/H_2O$ 7:3 at 0.250 mL/min. Method: Gradient: 5% B→95% B over 1.07 min. Flow: 4.5 mL/min. Detection: UV/Vis and/or ELSD, and MS, $t_R$ is given in min.

HPLC preparative: X-Bridge C18 5 µm, 50×19 mm ID from Waters. Eluents: A: $H_2O$+0.5% $NH_4OH$; B: $CH_3CN$; Gradient: 10% B→90% B over 5 min. Flow: 40.0 mL/min. Detection: UV/Vis and/or ELSD, and MS, $t_R$ is given in min.

HPLC chiral, analytical: (R,R) Whelk-O1 250×4.6 mm ID, 5 µm. Eluent A (80%): Heptane+0.05% DEA. Eluent B (20%): Ethanol+0.05% DEA. Flow: 0.8 mL/min. Detection: UV/Vis, $t_R$ is given in min.

NMR: Bruker Avance 400 (400 MHz); Varian Mercury 300 (300 MHz); chemical shifts are given in ppm relative to the solvent used; multiplicities: s=singlet, d=doublet, t=triplet, q=quadruplet, p=pentuplet, hex=hextet, hept=heptet, m=multiplet, br=broad, coupling constants are given in Hz.

The following examples illustrate the invention but do not at all limit the scope thereof.

Synthesis of Intermediates:

General Procedure A: Boc Deprotection

In a glass vial, under inert atmosphere (N₂), a solution of the Boc-protected amine (1.0 eq.) in CH₂Cl₂ was treated with 4N HCl in dioxane (10.0 eq.) and the reaction mixture was stirred at 0° C. or it until completion of the reaction. The reaction mixture was then concentrated under reduced pressure and the residue purified, when necessary, by FC or HPLC to give the desired compound.

Spiro[2.4]hepta-4,6-diene

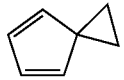

In a flame dried round-bottomed flask equipped with a magnetic stir bar and under inert atmosphere (N₂), a mixture of benzyltriethylammonium chloride (18.0 g, 78 mmol) in 50% aqueous NaOH solution (1.2 L) was heated to 45° C. A chilled solution of cyclopentadiene (formed by cracking of cyclopentadiene dimer at 180° C., 140 mL, 1.70 mol) in 1,2-dichloroethane (122 mL, 1.55 mol) was added to the stirred NaOH solution while keeping the internal temperature below 55° C. After completion of the addition (ca. 1.75 h), the reaction mixture was stirred at 50° C. for 2 h and allowed to cool down to rt. The layers were separated, the organic layer washed with 1M NaOH, dried (Na₂SO₄) and filtered. The crude brown liquid was distilled under reduced pressure (85-95 mbar) and the title compound was obtained as a colorless liquid (bp=45-50° C. at 80 mbar). $^1$H NMR (400 MHz, CDCl₃) δ 6.58 (m, 2H), 6.19 (m, 2H), 1.71 (s, 4H).

Diels Alder Reaction—Formation of (5R,6R)-5,6-bis-[(1-(1S)-ethoxycarbonyl)-ethoxy-carbonyl]-(4S,7R)-[4,7-ethenylene-spiro[2.4]heptane]

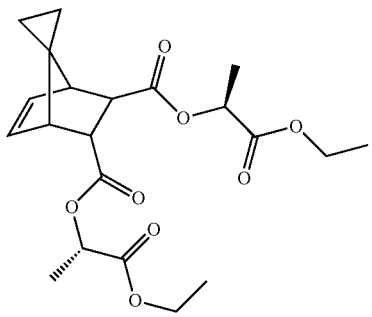 [SMILES: CCOC(=O)[C@H](C)OC(=O)C1C(C(=O)O[C@@H](C)C(=O)OCC)C2C=CC1C21CC1]

In a flame dried round-bottomed flask equipped with a magnetic stir bar and under inert atmosphere (N₂), to a solution of (E)-1,2-bis-[((1S)-1-ethoxycarbonylyethoxy-carbonyl]-ethene (7.40 g, 22.7 mmol) in n-hexane (76 mL) was added spiro[2.4]hepta-4,6-diene (3.14 g, 34.0 mmol) at rt. The reaction mixture was stirred at this temperature overnight. The mixture was concentrated under reduced pressure and the crude residue purified by FC (hept/EA, 9:1). The title compound was obtained as a pale yellow oil. TLC: rf (hept/EA, 9:1)=0.25. LC-MS-conditions 01: $t_R$=1.12 min; [M+H]⁺=409.00. $^1$H NMR (400 MHz, CDCl₃) δ 6.44 (dd, J=5.5, 3.0 Hz, 1 H), 6.32 (dd, J=5.5, 2.8 Hz, 1 H), 5.12 (q, J=7.1 Hz, 1 H), 5.06 (q, J=7.1 Hz, 1 H), 4.28-4.14 (m, 4 H), 3.76 (app. t, J=4.0 Hz, 1 H), 2.92 (d, J=4.8 Hz, 1 H), 2.86 (m, 1 H), 2.80 (m, 1 H), 1.55-1.47 (m, 6 H), 1.29 (t, J=7.3 Hz, 3 H), 1.29 (t, J=7.3 Hz, 3 H), 0.70 (m, 1 H), 0.56-0.44 (m, 3 H).

Saponification—Formation of (4S,7R)-[4,7-ethenylene-spiro[2.4]heptane]-(5R,6R)-5,6-bis-carboxylic acid

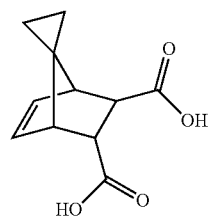 [SMILES: O=C(O)C1C(C(=O)O)C2C=CC1C21CC1]

To a solution of (5R,6R)-5,6-bis-[(1-(1S)-ethoxycarbonyl)-ethoxy-carbonyl]-(4S,7R)-[4,7-ethenylene-spiro[2.4]heptane] (9.51 g, 23.28 mmol) in THF/H₂O (1:1, 232 mL) was added LiOH (3.91 g, 93.13 mmol). The reaction mixture was stirred at rt overnight. 1N HCl was added in order to adjust the pH of the reaction mixture to pH=3, the layers separated and the aq. layer extracted with EA (3×). The combined org. extracts were dried over MgSO₄, filtered, and concentrated under reduced pressure. The crude residue was purified by FC (CH₂Cl₂/MeOH, 9:1) to give the title compound as a colorless oil. TLC: rf (CH₂Cl₂/MeOH, 9:1)=0.31. LC-MS-conditions 01: $t_R$=0.72 min; [M+CH₃CN+H]⁺= 250.18.

Iodolactonization—Formation of 6-iodo-2-oxohexahydrospiro[3,5-methanocyclopenta[b]furan-4,1'-cyclopropane]-7-carboxylic acid

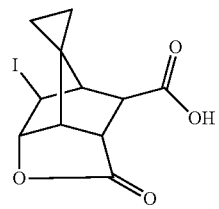 [SMILES: O=C(O)C1C2C(=O)OC3C(I)C1C1(CC1)C32]

To a solution of (4S,7R)-[4,7-ethenylene-spiro[2.4]heptane]-(5R,6R)-5,6-bis-carboxylic acid (5.60 g, 22.32 mmol) in CH₂Cl₂ (33 mL) were added NaHCO₃ (2.06 g, 24.56 mmol), water (100 mL), KI (1.37 g, 82.60 mmol) and I₂ (6.80 g, 26.79 mmol). The reaction mixture was stirred at rt for 3 h. The reaction was quenched by the addition of sat. aq. Na₂S₂O₃. The layers were separated and the aq. layer extracted with CH₂Cl₂ (3×). The combined org. extracts were dried over MgSO₄, filtered, and concentrated under reduced pressure. The crude foam was purified by FC (EA) to give the title compound as a white solid. TLC: rf (EA)= 0.33.

Esterification—Formation of methyl 6-iodo-2-oxo-hexahydrospiro[3,5-methanocyclopenta[b]furan-4,1'-cyclopropane]-7-carboxylate

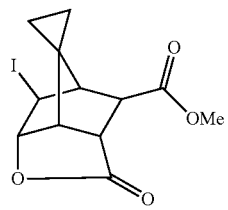 [SMILES: COC(=O)C1C2C(=O)OC3C(I)C1C1(CC1)C32]

In a flame dried round-bottomed flask equipped with a magnetic stir bar and under inert atmosphere (N₂), to a solution of 6-iodo-2-oxohexahydrospiro[3,5-methanocyclopenta[b]furan-4,1'-cyclopropane]-7-carboxylic acid (5.00 g, 14.96 mmol) in dry MeOH (75 mL) was added TMSCH₂N₂ (2.0 M in hexanes, 37.0 mL, 74.83 mmol). The reaction mixture was stirred at rt overnight, concentrated under reduced pressure and purified by FC (hept/EA, 4:1) to give the title compound as a white solid. TLC: rf (hept/EA, 4:1)=0.18.

Retro-Iodolactonization—Formation of (6R)-6-methoxycarbonyl-(4S,7R)-[4,7-ethenylene-spiro[2.4]heptane]-(5R)-5-carboxylic acid

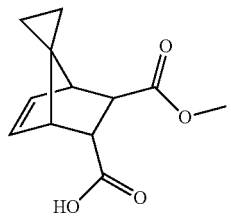 [SMILES: COC(=O)C1C(C(=O)O)C2C=CC1C21CC1]

In a flame dried round-bottomed flask equipped with a magnetic stir bar and under inert atmosphere (N₂), to a solution of methyl 6-iodo-2-oxohexahydrospiro[3,5-methanocyclopenta[b]furan-4,1'-cyclopropane]-7-carboxylate (2.86 g, 8.21 mmol) in acetic acid (29 mL) was added zinc powder (8.06 g, 123.23 mmol). The reaction mixture was stirred at 65° C. for 4 h, cooled down to rt, filtered and partitioned between water and EA. The layers were separated and the aq. layer extracted with EA (3×). The combined org. extracts were washed with brine, dried over MgSO₄, filtered, and concentrated under reduced pressure. The crude residue was purified by FC (hept/EA, 1:1) and the title compound was obtained as a colorless oil. TLC: rf (hept/EA, 1:1)=0.41.

Double Bond Reduction—Formation of (6R)-6-methoxycarbonyl-(4S,7R)-[4,7-ethylene-spiro[2.4]heptane]-(5R)-5-carboxylic acid

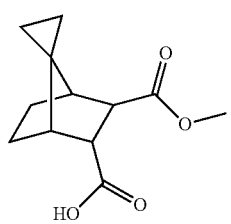 [SMILES: COC(=O)C1C(C(=O)O)C2CCC1C21CC1]

In a flame dried round-bottomed flask equipped with a magnetic stir bar and under inert atmosphere (N₂), a deoxygenated suspension of (6R)-6-methoxycarbonyl-(4S,7R)-[4,7-ethenylene-spiro[2.4]heptane]-(5R)-5-carboxylic acid (220 mg, 0.99 mmol), Pd/C 10% (44 mg) and cyclohexene (0.20 mL, 1.98 mmol) in dry THF (2.5 mL) was stirred at reflux for 2 h. The reaction mixture was filtered through celite and the filter cake washed with THF. The filtrate was concentrated under reduced pressure and the title compound obtained as a white solid. TLC: rf (hept/EA, 2:3)=0.48.

2-(Chloromethyl)oxazole-4-carbaldehyde

In a flame dried round-bottomed flask equipped with a magnetic stir bar and under inert atmosphere (N₂), to a at −78° C. cooled solution of methyl 2-(chloromethyl)oxazole-4-carboxylate (25.00 g, 142.00 mmol) in CH₂Cl₂ (475 mL) was added a 1M diisobutylaluminum hydride solution in CH₂Cl₂ (285.00 mL, 285.00 mmol). The reaction mixture was stirred for 3 h at −78° C. Methanol (125 mL) was carefully added and the reaction mixture was warmed to rt. The reaction mixture was then diluted with CH₂Cl₂ (500 mL) and washed with a sat. aq. solution of Rochelle salt. The organic layer was dried over MgSO₄, filtered, and the solvent removed under reduced pressure to give the title compound as orange oil. LC-MS-conditions 02: $t_R$=0.40 min; [M+CH3CN+H]⁺=187.44.

1-(2-(Chloromethyl)oxazol-4-yl)ethanol

In a flame dried round-bottomed flask equipped with a magnetic stir bar and under inert atmosphere (N₂), a solution of 2-(chloromethyl)oxazole-4-carbaldehyde (18.10 g, 124.36 mmol) in CH₂Cl₂ (625 mL) was treated at 0° C. with trimethylaluminum (311.00 mL of a 2 M solution in heptane, 621.80 mmol). The reaction mixture was then stirred at 0° C. for 60 min. Sat. aq. NH₄Cl was then added and the aq. layer was extracted twice with CH₂Cl₂ and twice with EA. The combined org. extracts were dried over MgSO₄, filtered, and the solvents were removed under reduced pressure. The crude residue was purified by FC (hept/EA, 3:7) and the title compound obtained as a yellow oil. TLC: rf (hept/EA, 3:7)=0.38. LC-MS-conditions 02: $t_R$=0.43 min, [M+H]⁺=162.12.

1-(2-(Chloromethyl)oxazol-4-yl)ethanone

In a flame dried round-bottomed flask equipped with a magnetic stir bar and under inert atmosphere (N₂), a solution of 1-(2-(chloromethyl)oxazol-4-yl)ethanol (14.90 g, 92.20 mmol) in AcCN (458 mL) was treated at rt with MnO₂ (44.54 g, 461.00 mmol). The reaction mixture was stirred for 5 h at rt before being filtered through Celite. The solvent was removed under reduced pressure. The crude residue was purified by MPLC (hept/EA,1:1) and the title compound obtained as a white solid. TLC: rf (hept/EA, 1:1)=0.50. LC-MS-conditions 02: $t_R$=0.47 min, [M+H]⁺=160.11.

2-(Chloromethyl)-4-(1,1-difluoroethyl)oxazole

In a flame dried round-bottomed flask equipped with a magnetic stir bar and under inert atmosphere (N₂), 1-(2-(chloromethyl)oxazol-4-yl)ethanone (1.55 g, 9.71 mmol) in CH₂Cl₂ (2.5 mL) was treated with Deoxo-Fluor (14.30 mL of a 50% solution in toluene, 38.90 mmol) and stirred at 45° C. for 72 h. The solution was cooled to 0° C., aq. 1 M NaOH (35 mL) was added carefully (exotermic) and the resulting mixture was diluted with CH₂Cl₂. The layers were separated and the organic layer was washed with sat. aq. NaCl and water, dried over MgSO₄, filtered, and the solvent removed under reduced pressure. The residue was purified by FC (hept/IpAc 5:1) to give the title compound as yellow oil. LC-MS-conditions 03: $t_R$=0.72 min, [M+H]$^+$=182.06.

2-(Azidomethyl)-4-(1,1-difluoroethyl)oxazole

In a round-bottomed flask equipped with a magnetic stir bar and under inert atmosphere (N$_2$), sodium azide (380 mg, 5.78 mmol) was added to a solution of 2-(chloromethyl)-4-(1,1-difluoroethyl)oxazole (1.00 g, 5.51 mmol) in DMF (25 mL) and heated to 80° C. for 4 h. The reaction mixture was diluted with water and extracted with Et$_2$O. The organic phase was dried over MgSO$_4$, filtered, and the solvent removed under reduced pressure to give the title compound as a yellow oil. LC-MS-conditions 04: $t_R$=0.73 min, [M+H]$^+$=189.35.

(4-(1,1-Difluoroethyl)oxazol-2-yl)methanamine

In a round-bottomed flask equipped with a magnetic stir bar and condenser, to a solution of 2-(azidomethyl)-4-(1,1-difluoroethyl)oxazole (1.253 g, 6.66 mmol) in THF (90 ml) was added triphenylphosphine on polystyrene (1.60 mmol/g 100-200 mesh, 2.096 g, 7.99 mmol) and water (5 mL). The resulting mixture was heated to 60° C. for 3 h. The mixture was filtered and the filtrate was dried over MgSO$_4$, filtered, and the solvent removed under reduced pressure to give the title compound. LC-MS-conditions 04: $t_R$=0.24 min, [M+H]$^+$=163.21.

Coupling with (4-(1,1-difluoroethyl)oxazol-2-yl) methanamine—Formation of (1R,2R,3R,4S)-Methyl 3-(((4-(1,1-difluoroethyl)oxazol-2-yl) methyl)carbamoyl)spiro[bicyclo[2.2.1]heptane-7,1'-cyclopropane]-2-carboxylate

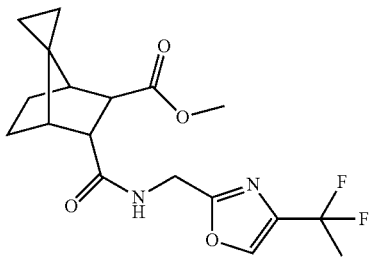 [SMILES: COC(=O)C1C(C(=O)NCc2nc(C(C)(F)F)co2)C2CCC1C21CC1]

In a flame dried round-bottomed flask equipped with a magnetic stir bar and under inert atmosphere (N$_2$), to a solution of (6R)-6-methoxycarbonyl-(4S,7R)-[4,7-ethylenespiro[2.4]heptane]-(5R)-5-carboxylic acid (1.00 g, 4.46 mmol) in dry CH$_2$Cl$_2$ (16 mL) were added 3 drops of DMF and oxalyl chloride (0.426 mL, 4.93 mmol). The reaction mixture was stirred at rt for 60 minutes and concentrated under reduced pressure. To a solution of (4-(1,1-difluoroethyl)oxazol-2-yl)methanamine (0.723 g, 4.46 mmol) in pyridine (1.08 mL) was added a solution of the acyl chloride in acetone (6 mL). The reaction mixture was stirred at rt for 1 h, diluted with EA and successively washed with aq. 1N HCl, sat. aq. NaHCO$_3$ and brine. The org. layer was dried over MgSO$_4$, filtered, and concentrated under reduced pressure. The residue was purified by FC (hept->hept/EA, 7:3) to give the title compound as yellow oil. LC-MS-conditions 04: $t_R$=0.84 min; [M+H]$^+$=369.20.

(1R,2R,3R,4S)-3-(((4-(1,1-Difluoroethyl)oxazol-2-yl) methyl)carbamoyl)spiro[bicyclo[2.2.1]heptane-7, 1'-cyclopropane]-2-carboxylic acid

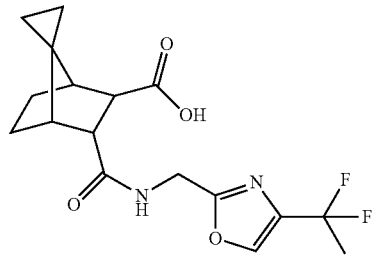 [SMILES: CC(F)(F)c1coc(CNC(=O)C2C(C(=O)O)C3CCC2C32CC2)n1]

To a solution of (1R,2R,3R,4S)-methyl 3-(((4-(1,1-difluoroethyl)oxazol-2-yl)methyl)carbamoyl)spiro[bicyclo[2.2.1] heptane-7,1'-cyclopropane]-2-carboxylate (1.27 g, 3.45 mmol) in THF (20 mL) was added aq. 2N NaOH (16.00 mL, 32.00 mmol). The reaction mixture was stirred at rt until completion of the reaction. The mixture was then poured into aq. 1N HCl and extracted with EA (3×). The combined org. extracts were washed with brine, dried over MgSO$_4$, filtered, and concentrated under reduced pressure to give the title compound as white foam. LC-MS-conditions 04: $t_R$=0.75 min; [M+H]$^+$=355.25.

tert-Butyl 3-fluoro-4-oxopiperidine-1-carboxylate

In a flame dried round-bottomed flask equipped with a magnetic stir bar and under inert atmosphere (N$_2$), to a solution of tert-butyl 4-oxopiperidine-1-carboxylate (5.00 g, 25.09 mmol) in dry DMF (25 mL) was added trimethylsilyl chloride (5.77 mL, 45.17 mmol) followed by Et$_3$N (8.38 mL, 60.23 mmol) at rt. The reaction mixture was stirred at 80° C. for 24 h. The mixture was then cooled to rt, diluted with hexanes and washed with sat. aq. NaHCO$_3$. The layers were separated and the org. layer dried over MgSO$_4$, filtered, and concentrated under reduced pressure. The residue was purified by FC (hexanes/EA, 9:1) to afford tert-butyl 4-((trimethylsilyl)oxy)-5,6-dihydropyridine-1(2H)-carboxylate as colorless oil. TLC: rf (Hexanes/EA, 9:1)=0.50.

In a flame dried round-bottomed flask equipped with a magnetic stir bar and under inert atmosphere (N$_2$), to a solution of tert-butyl 4-((trimethylsilyl)oxy)-5,6-dihydropyridine-1(2H)-carboxylate (5.00 g, 18.40 mmol) in dry acetonitrile (25 mL) was added 1-(chloromethyl)-4-fluoro-1,4-diazoniabicyclo[2.2.2]octane ditetrafluoroborate (7.55 g, 20.3 mmol) at rt. The reaction mixture was stirred at rt for 2 h then poured into EA and successively washed with aq. 1% NaHCO$_3$ and brine. The org. layer was dried over MgSO$_4$, filtered, and concentrated under reduced pressure. The residue was purified by FC (hexanes/EA, 4:1) to afford the title compound as a pale yellow solid. LC-MS-conditions 03: $t_R$=0.55 min; [M–CH$_3$+H]$^+$=203.23; TLC: rf (hexanes/EA, 4:1)=0.17.

trans-tert-Butyl 4-amino-3-fluoropiperidine-1-carboxylate and cis-tert-butyl 4-amino-3-fluoropiperidine-1-carboxylate In a flame dried round-bottomed flask equipped with a magnetic stir bar and under inert atmosphere (N$_2$), to a solution of tert-butyl 3-fluoro-4-oxopiperidine-1-carboxylate (0.80 g, 3.68 mmol) in MeOH (10 mL) was added ammonium acetate (1.99 g, 25.80 mmol) and the resulting solution stirred at rt for 2 h. NaCNBH$_3$ (0.29 g, 4.42 mmol) was then added and the solution stirred at rt overnight. The reaction mixture was concentrated to dryness and the organics extracted with EA from a 1% aq. solution of Na$_2$CO$_3$. The combined organic extracts were washed with brine, dried over MgSO$_4$, filtered and concentrated under reduced pressure. The residue was purified with FC (CH$_2$Cl$_2$/MeOH, 9:1) to afford trans-tert-butyl 4-amino-3-fluoropiperidine-1-carboxylate as first eluting diastereomer and cis-tert-butyl 4-amino-3-fluoropiperidine-1-carboxylate as second eluting diastereomer both as colorless oils which solidified upon standing. Trans diastereomer: LC-MS-conditions 03: $t_R$=0.48 min; [M–CH$_3$+H]$^+$=204.25; TLC: rf (CH$_2$Cl$_2$/MeOH, 9:1)=0.30. Cis diastereomer: LC-MS-conditions 03: $t_R$=0.46; [M+H]$^+$=219.26; TLC: rf (CH$_2$Cl$_2$/MeOH, 9:1)=0.09.

PREPARATION OF EXAMPLES tert-Butyl 4-((1R,2R,3R,4S)-3-(((4-(1,1-difluoroethyl)oxazol-2-yl) methyl)carbamoyl)spiro[bicyclo[2.2.1]heptane-7,1'-cyclopropan]-2-ylcarboxamido)-3,4-trans-fluoropiperidine-1-carboxylate

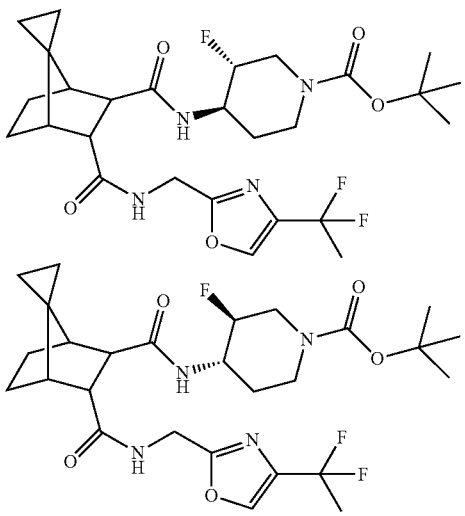

In a flame dried round-bottomed flask equipped with a magnetic stir bar and under inert atmosphere (N$_2$), to a solution of (1R,2R,3R,4S)-3-(((4-(1,1-difluoroethyl)oxazol-2-yl)methyl)carbamoyl)spiro[bicyclo[2.2.1]heptane-7,1'-cyclopropane]-2-carboxylic acid (0.200 g, 0.564 mmol) in CH$_2$Cl$_2$ (8.5 mL) was added trans-tert-butyl 4-amino-3-fluoropiperidine-1-carboxylate (0.148 g, 0.677 mmol), EDC HCl (0.224 g, 1.130 mmol), HOBt (0.092 g, 0.68 mmol) and DIPEA (0.29 mL, 1.69 mmol). The reaction mixture was stirred at rt until completion of the reaction. Water was then added, the layers separated and the org. layer dried over MgSO$_4$, filtered, and concentrated under reduced pressure. The diastereomers were separated by FC (EA/Hexanes, 7:3). First eluting diastereomer: LC-MS-conditions 04: $t_R$=0.90 min; [M+H]$^+$=555.29; TLC: rf (hexanes/EA, 3:7)=0.54. Second eluting diastereomer: LC-MS-conditions 04: $t_R$=0.90 min; [M+H]$^+$=555.30; TLC: rf (hexanes/EA, 3:7)=0.35.

Example 1

(1S,2R,3R,4R)—N$^2$—((4-(1,1-Difluoroethyl)oxazol-2-yl)methyl)-N$^3$-(trans-3-fluoropiperidin-4-yl)spiro[bicyclo[2.2.1]heptane-7,1'-cyclopropane]-2,3-dicarboxamide(diastereoisomer 1)

Following general procedure A starting from the first eluting diastereoisomer tert-butyl 4-((1R,2R,3R,4S)-3-(((4-(1,1-difluoroethyl)oxazol-2-yl) methyl)carbamoyl)spiro[bicyclo[2.2.1]heptane-7,1'-cyclopropan]-2-ylcarboxamido)-3,4-trans-fluoropiperidine-1-carboxylate. LC-MS-conditions 04: $t_R$=0.62 min; [M+H]$^+$=455.28. HPLC chiral, analytical: $t_R$=15.91 min.

Example 2

(1S,2R,3R,4R)—N$^2$—((4-(1,1-Difluoroethyl)oxazol-2-yl)methyl)-N$^3$-(trans-3-fluoropiperidin-4-yl)spiro[bicyclo[2.2.1]heptane-7,1'-cyclopropane]-2,3-dicarboxamide(diastereoisomer 2)

Following general procedure A starting from the second eluting diastereoisomer tert-butyl 4-((1R,2R,3R,4S)-3-(((4-(1,1-difluoroethyl)oxazol-2-yl)methyl)carbamoyl)spiro[bicyclo[2.2.1]heptane-7,1'-cyclopropan]-2-ylcarboxamido)-3,4-trans-fluoropiperidine-1-carboxylate. LC-MS-conditions 04: $t_R$=0.61 min; [M+H]$^+$=455.29. HPLC chiral, analytical: $t_R$=13.043 min.

II. Biological Assays

FLIPR Assay (ALX Receptor)

Experimental Method:

Intracellular Calcium Measurements:

Cells expressing recombinant human ALX receptor and the G-protein Gα16 (HEK293-hALXR-Gα16) were grown to 80% confluency in Growing Medium (GM). Cells were detached from culture dishes with a cell dissociation buffer (Invitrogen, 13151-014), and collected by centrifugation at 1,000 rpm at rt for 5 min in Assay Buffer (AB) (equal parts of Hank's BSS (Gibco, 14065-049) and DMEM without Phenol Red (Gibco, 11880-028)). After 60 min incubation at 37° C. under 5% CO$_2$ in AB supplemented with 1 μM Fluo-4 (AM) (Invitrogen, F14202) and 20 mM HEPES (Gibco, 15630-056), the cells were washed and resuspended in AB. They were then seeded onto 384-well FLIPR assay plates (Greiner, 781091) at 50,000 cells in 70 μl per well and sedimented by centrifugation at 1,000 rpm for 1 min. Stock solutions of test compounds were made up at a concentration of 10 mM in DMSO, and serially diluted in AB to concentrations required for activation dose response curves. WKYMVm (Phoenix Peptides) was used as a reference agonist. A FLIPR Tetra instrument (Molecular Devices) was operated according to the manufacturer's standard instructions, adding 4 μl of test compound dissolved at 10 mM in DMSO and diluted prior to the experiment in assay buffer to obtain the desired final concentration. Changes in fluorescence were monitored before and after the addition of test compounds at lex=488 nm and lem=540 nm. Emission peak values above base level after compounds addition were exported after base line subtraction. Values were normalized to high-level control (WKYMVm compound, 10 nM final concentration) after subtraction of the base line value (AB addition).

Agonistic activities with respect to the ALX receptor (EC$_{50}$ values, median of n replications) of exemplified compounds are displayed in Table 1.

TABLE 1

| Compound | EC$_{50}$ [nM] |
| --- | --- |
| Example 1: (1S,2R,3R,4R)-N$^2$-((4-(1,1-Difluoroethyl)oxazol-2-yl)methyl)-N$^3$-(trans-3-fluoropiperidin-4-yl)spiro[bicyclo[2.2.1]heptane-7,1'-cyclopropane]-2,3-dicarboxamide (diastereomer 1) | 6.6 (n = 6) |
| Example 2: (1S,2R,3R,4R)-N$^2$-((4-(1,1-Difluoroethyl)oxazol-2-yl)methyl)-N$^3$-(trans-3-fluoropiperidin-4-yl)spiro[bicyclo[2.2.1]heptane-7,1'-cyclopropane]-2,3-dicarboxamide (diastereoisomer 2) | 3.6 (n = 8) |

FLIPR Assay (FPR1 Receptor)
Experimental Method:
Intracellular Calcium Measurements:
Cells expressing recombinant human FPR1 receptor and the G-protein Gα16 (HEK293-hFPR1-Gα16) were grown to 80% confluency in Growing Medium (GM). Cells were detached from culture dishes with a cell dissociation buffer (Invitrogen, 13151-014), and collected by centrifugation at 1,000 rpm at rt for 5 min in Assay Buffer (AB) (equal parts of Hank's BSS (Gibco, 14065-049) and DMEM without Phenol Red (Gibco, 11880-028)). After 60 min incubation at 37° C. under 5% $CO_2$ in AB supplemented with 1 µM Fluo-4 (AM) (Invitrogen, F14202) and 20 mM HEPES (Gibco, 15630-056), the cells were washed and resuspended in AB. They were then seeded onto 384-well FLIPR assay plates (Greiner, 781091) at 50,000 cells in 70 µl per well and sedimented by centrifugation at 1,000 rpm for 1 min. Stock solutions of test compounds were made up at a concentration of 10 mM in DMSO, and serially diluted in AB to concentrations required for activation dose response curves. WKYMVm (Phoenix Peptides) was used as a reference agonist. A FLIPR Tetra instrument (Molecular Devices) was operated according to the manufacturer's standard instructions, adding 4 µl of test compound dissolved at 10 mM in DMSO and diluted prior to the experiment in assay buffer to obtain the desired final concentration. Changes in fluorescence were monitored before and after the addition of test compounds at lex=488 nm and lem=540 nm. Emission peak values above base level after compounds addition were exported after base line subtraction. Values were normalized to high-level control (WKYMVm compound, 10 nM final concentration) after subtraction of the base line value (AB addition).

Agonistic activities with respect to the FPR1 receptor (EC$_{50}$ values, median of n replications) of exemplified compounds are displayed in Table 1.

TABLE 2

| Compound | EC$_{50}$ [nM] |
| --- | --- |
| Example 1: (1S,2R,3R,4R)-N$^2$-((4-(1,1-Difluoroethyl)oxazol-2-yl)methyl)-N$^3$-(trans-3-fluoropiperidin-4-yl)spiro[bicyclo[2.2.1]heptane-7,1'-cyclopropane]-2,3-dicarboxamide (diastereomer 1) | >6000 (n = 4) |
| Example 2: (1S,2R,3R,4R)-N$^2$-((4-(1,1-Difluoroethyl)oxazol-2-yl)methyl)-N$^3$-(trans-3-fluoropiperidin-4-yl)spiro[bicyclo[2.2.1]heptane-7,1'-cyclopropane]-2,3-dicarboxamide (diastereoisomer 2) | >7000 (n = 5) |

Plasma Stability Assay
Rat or human serum adjusted at pH 7.4 with lactic acid or ammonium hydroxide, were equilibrated at 37° C. under orbital shaking in an incubator containing 5% $CO_2$. The reaction was initiated by the addition of 1 µM of compounds (1 µl of 1 mM stock solution in DMSO in 999 µl of plasma). At 0.01 h, 0.25 h, 0.5 h, 1 h, 2 h, 4 h and 6 h aliquots (30 µl) were transferred in a 96 well plate containing 90 µl MeOH placed on ice to stop the reaction. After vortexing for 20 min at 1400 rpm on an Eppendorf thermomixer, the plates were centrifuged at 3220 g for 20 min at 4° C. and the supernatants were analyzed with LC-MS/MS. Calibration samples in serum containing 0.1% of dichlorvos (2,2-dichlorovinyl-dimethyl-phosphate) were prepared and analysed in parallel to the incubation samples to allow the quantification. Half lives ($T_{1/2}$) in hours were then calculated. In addition the remaining concentration of the respective compound after time $T_{last}$ relative to the concentration at the beginning has been determined (table 3).

TABLE 3 stability in serum

| compound | number of replicates | species | $T_{1/2}$ [h] | $T_{last}$ [h] | remaining concentration at $T_{last}$ [%] |
| --- | --- | --- | --- | --- | --- |
| example 1 | 1 | human | >6 | 6 | 97 |
| example 1 | 1 | rat | >6 | 6 | >100 |
| example 2 | 1 | human | >6 | 6 | >100 |
| example 2 | 1 | rat | >6 | 6 | >100 |

Plasma Protein Binding Assay
Compounds were added to human plasma adjusted at pH 7.4 with lactic acid or ammonium hydroxide (final concentration 1 µM) and dialyzed with RED (Rapid Equilibrium Dialysis) devices against Phosphate Buffered Saline (0.1M sodium Phosphate and 0.15 M sodium chloride) 0.1 M pH 7.4 for 4 h at 37° C. in an incubator containing 5% $CO_2$. Following dialysis, an aliquot of plasma and buffer were diluted with an equal volume of the opposite matrix to nullify the matrix effect and a calibration was prepared in the mixed matrix. Aliquots of samples and calibrations (30 µl) were transferred in a 96 well plate containing 90 µl MeOH to precipitate the proteins. After vortexing for 20 min at 1400 rpm on an Eppendorf thermomixer, the plates were centrifuged at 3220 g for 20 min at 4° C. and the supernatants were analyzed with LC-MS/MS. Concentrations of analyte were used for the calculation of the fraction bound to plasma. Propranolol [(±)-1-isopropylamino-3-(1-naphthyloxy)-2-propanol], a reference compound, was run in parallel.

| compound | number of replicates | species | Plasma protein binding (%) |
| --- | --- | --- | --- |
| example 1 | 3 | human | 54.8 |
| example 1 | 3 | rat | 50.7 |
| example 2 | 3 | human | 63.8 |
| example 2 | 3 | rat | 47.7 |

The invention claimed is:
1. A compound of formula (I)

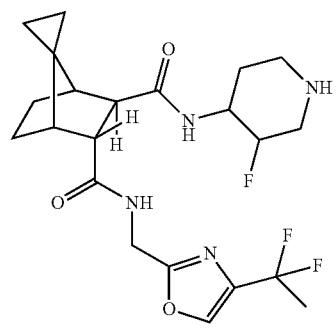

(I)

wherein the substituents at the piperidine ring are in trans-arrangement;
or a salt of the compound.

2. The compound of claim 1, wherein the compound has a formula (I$_{ST1}$),

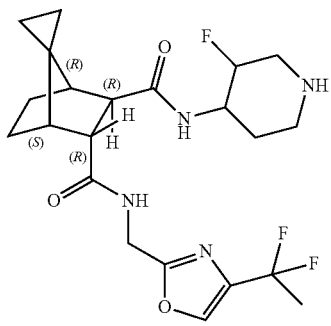

(I$_{ST1}$)

wherein the substituents at the piperidine ring are in trans-arrangement;
or a salt of the compound.

3. The compound of claim 1, wherein the compound is (1S,2R,3R,4R)—N$^2$—((4-(1,1-difluoroethyl)oxazol-2-yl) methyl)—N$^3$—((3S,4S)-3-fluoropiperidin-4-yl)spiro[bicyclo[2.2.1]heptane-7,1'-cyclopropane]-2,3-dicarboxamide;
or a salt of the compound.

4. The compound of claim 1, wherein the compound is (1S,2R,3R,4R)—N$^2$—((4-(1,1-difluoroethyl)oxazol-2-yl) methyl)—N$^3$—((3R,4R)-3-fluoropiperidin-4-yl)spiro [bicyclo [2.2.1]heptane-7,1'-cyclopropane]-2,3 -dicarboxamide;
or a salt of the compound.

5. A pharmaceutical composition comprising, as active principle, the compound of claim 1, or a pharmaceutically acceptable salt thereof, and at least one therapeutically inert excipient.

6. A method of treating a disease comprising administering to a subject in need thereof a compound of claim 1 or a pharmaceutically acceptable salt thereof, wherein the disease includes rheumatoid arthritis, acute lung injury, asthma, cystic fibrosis, inflammatory bowel disease, keratoconjunctivitis sicca, HIV-mediated retroviral infections, atopic dermatitis, pulmonary fibrosis or Alzheimer's disease.

7. A method of treating a disease comprising administering to a subject in need thereof a pharmaceutical composition according to claim 5, wherein the disease includes rheumatoid arthritis, acute lung injury, asthma, cystic fibrosis, inflammatory bowel disease, keratoconjunctivitis sicca, HIV-mediated retroviral infections, atopic dermatitis, pulmonary fibrosis or Alzheimer's disease.

* * * * *